United States Patent

Mills

Patent Number: 6,059,779
Date of Patent: May 9, 2000

[54] DELIVERY CATHETER FOR ELECTROLYTICALLY DETACHABLE IMPLANT

[75] Inventor: Timothy Mills, Tiberon, Calif.

[73] Assignee: Target Therapeutics, Inc., Fremont, Calif.

[21] Appl. No.: 08/546,516

[22] Filed: Oct. 20, 1995

Related U.S. Application Data

[63] Continuation-in-part of application No. 08/430,744, Apr. 28, 1995, abandoned.

[51] Int. Cl.$^7$ .................................................. A61B 17/36
[52] U.S. Cl. ........................... 606/41; 600/373; 600/378; 600/381
[58] Field of Search ................................. 606/28, 32, 41, 606/45; 600/372–373, 377–378, 381, 585

[56] References Cited

U.S. PATENT DOCUMENTS

| | | |
|---|---|---|
| 3,868,956 | 3/1975 | Alfidi et al. . |
| 4,682,596 | 7/1987 | Bales et al. . |
| 4,920,980 | 5/1990 | Jackowski ............................ 128/658 X |
| 5,354,295 | 10/1994 | Guglielmi et al. .................... 606/41 X |

FOREIGN PATENT DOCUMENTS

| | | |
|---|---|---|
| 2115289 | 9/1983 | United Kingdom . |
| WO 93/16650 | 9/1993 | WIPO . |
| WO 94/16632 | 8/1994 | WIPO . |

*Primary Examiner*—Cary O'Connor
*Assistant Examiner*—Ryan Carter
*Attorney, Agent, or Firm*—Morrison & Foerster LLP

[57] ABSTRACT

The invention involves a catheter for introducing a delivery member such as a guidewire having an implant coupled thereto via an electrolytically disintegratable link that is coupled to the anode of a power supply having an anode and a cathode. The catheter comprises an elongated tubular member having an outer surface, proximal and distal end portions, a lumen extending between those portions, an electrode and a conductor. The electrode is disposed within the outer surface of the tubular member in the vicinity of the distal end portion and has a surface that faces and communicates with the lumen. The electrode is electrically coupled to the conductor which, in turn, is adapted for coupling to the power supply cathode such that when the electrolytically disintegratable link is placed in an ionic solution, such as can be found in an aneurysm, and positive current is provided from the power supply to the link, current from the link may return to the cathode of the power supply via the electrode. With this construction, the electrode is shielded from endolumenal structures which could otherwise increase the resistance in the current path from the sacrificial link to the electrode. The positioning of the electrode in the catheter as described above allows a reproducible impedance path from the electrode to the detachment zone, thus reducing detachment time variability.

37 Claims, 6 Drawing Sheets

DELIVERY CATHETER FOR ELECTROLYTICALLY DETACHABLE IMPLANT

This application is a continuation-in-part of U.S. patent application Ser. No. 08/430,744 filed on Apr. 28, 1995, now abandoned.

FIELD OF THE INVENTION

The invention generally relates to the delivery of an occlusion device to a desired site in a mammal to facilitate the formation of mechanical blockage or thrombin in arteries, veins, aneurysms, vascular malformations, and arteriovenous fistulas. More specifically, the invention involves apparatus for facilitating electrolytic separation of an implant, such as an embolic device, from a delivery member.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach which involves surgery or microsurgery. This treatment is common with intracranial berry aneurysms. The method comprises clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure is the extra-intravascular approach. This approach involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated herein by reference.

A still further approach, the least invasive, also is described in Guglielmi et al (supra). It is the endovascular approach. In this approach, the interior of the aneurysm is entered by use of a catheter such as those shown in Engelson (Catheter Guidewire), U.S. Pat. No. 4,884,579 and also in Engelson (Catheter for Guidewire Tracking), U.S. Pat. No. 4,739,768. These patents describe devices utilizing guidewires and catheters which allow access to an aneurysm from remote portions of the body. Specifically, by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of difficulty in introducing the balloon into the aneurysm sac, the possibility of an aneurysm rupture due to overinflation of the balloon within the aneurysm or due to stress placed on the nonspherically shaped aneurysm by the spherical balloon, and the risk associated with traction produced when detaching the balloon.

A highly desirable embolism-forming device that may be introduced into an aneurysm using endovascular placement procedures, is found in U.S. Pat. No. 4,994,069, to Ritchart et al. The device, typically a platinum/tungsten alloy coil having a very small diameter, may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136), discussed above.

Guglielmi et al. shows an embolism-forming device and procedure for using that device. Specifically, the Guglielmi device fills a vascular cavity (such as an aneurysm) with an embolic device, typically a platinum coil, that has been endovascularly delivered. The coil is then severed from its insertion tool by the application of a small electric current. Desirably, the insertion device involves a guidewire which is attached at its distal end to the embolic device by a sacrificial joint that is electrolytically dissolvable. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety of ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

U.S. patent application Ser. No. 5,423,829, describes a variation of the Guglielmi detachable coil using an improved sacrificial link between the guidewire and the coil. The size of the sacrificial link is limited to allow more precise placement of the embolic device and facilitate quick detachment. The focussed electrolysis found at the sacrificial site reduces the overall possibility of occurrence of multiple electrolysis sites and liberation of large particles from those sites.

The circuit involved in the electrolytic coil detachment arrangements discussed above generally includes a power source having its positive terminal coupled to the sacrificial link via a guidewire, for example. More specifically, a positive electric current of approximately 0.01 to 2 milliamps is applied to the guidewire which is coupled to the sacrificial link that is intended to undergo electrolytic disintegration and which initially couples the implant (e.g., the vasoocclusion device) to the guidewire. The negative terminal of the power source is typically coupled to an electrode that is placed over and in contact with the patient's skin. This can be accomplished, for example, with a large skin electrode such as a ground pad or needle. Thus, the current path flowing from the detachment zone (etch site on the sacrificial link) to the ground electrode includes the patient's fluids and tissues. While the impedance to current flow is generally predictable through the delivery member or guidewire (approximately 200 ohms), the additional impedance of the current's return path to the ground electrode is dependent on variable impedances which depend on the blood milieu of the aneurysm, density of coil packing in the aneurysm, conductivity of the aneurysm wall, patient's tissue and return skin electrode, and fluid volume, for example. If, due to the variable impedances, the impedance to current flow through the occlusive device, which preferably is a platinum coil, becomes less than the impedance to current flow from the detachment zone, it is believed that detachment times will increase.

Another return electrode or cathode arrangement is disclosed in U.S. Pat. No. 5,354,295 to Guglielmi et al. In that arrangement, the microcatheter is supplied with an end electrode. More specifically, the electrode extends distally from the microcatheter and is coupled to an electrical conductor or wire disposed along the length of the microcatheter. The wire is ultimately led back to the negative terminal of the power source so that the electrode (ring electrode) is used as the cathode during electrothrombosis instead of an exterior skin electrode.

According to the '295 patent, the electrical currents and electrical current paths which are set up during electrothrombosis formation using the above-described catheter-electrode arrangement are local to the site of application, which allows even smaller currents and voltages to be used to initiate electrothrombosis than in the situation when an exterior skin electrode must be utilized. The electrothrombosic current distributions are also better controlled and localized to the site of the thrombus formation. The possibility of stray thrombus formations occurring at unwanted sites or uncontrolled and possibly unwanted electrical current patterns being established elsewhere in the brain or body is therefore largely avoided.

However, Applicant has found that under certain conditions, this return electrode arrangement may not provide consistent results. For example, since the return electrode or cathode extends distally from the microcatheter and is directly exposed to the endolumenal environment, it can contact tissue in that environment, such as the wall of the aneurysm. It is believed that such contact would increase the resistance in the current return path from the sacrificial link to the return electrode and increase electrolytic detachment times. In addition, multiple coils typically are placed in the aneurysm to increase the packing density therein and enhance thrombosis. Coils previously placed within the aneurysm may contact the electrode as the microcatheter is positioned at the aneurysm opening to deliver a further coil. It is believed that this may result in the current finding a lower impedance return path through portions of contacting coils than through the blood or fluid between the sacrificial link and the electrode. This may preclude the necessary electrolysis for disintegration of the sacrificial link, since optimal electrolysis occurs when the fluid resistance is less than the coil resistance.

SUMMARY OF THE INVENTION

The present invention involves a catheter for introducing a delivery member such as a guidewire having an implant coupled thereto via an electrolytically disintegratable link that is coupled to the anode of a power supply having an anode and a cathode. According to the invention, the catheter comprises an elongated tubular member having an outer surface, proximal and distal end portions, a lumen extending between those portions, an electrode and a conductor. The electrode is disposed within the outer surface of the tubular member in the vicinity of the distal end portion and has a surface that faces and communicates with the lumen. The electrode is electrically coupled to the conductor which, in turn, is adapted for coupling to the power supply cathode such that when the electrolytically disintegratable link is placed in an inoic solution, such as can be found in an aneurysm, and positive current is provided from the power supply to the link, current from the link may return to the cathode of the power supply via the electrode. With this construction, the electrode is shielded from endolumenal structures which could otherwise increase the resistance in the current path from the sacrificial link to the electrode. The positioning of the electrode in the catheter as described above allows a reproducible impedance path from the electrode to the detachment zone, thus reducing detachment time variability.

In one embodiment, the electrode also is spaced inwardly from the distal tip of the catheter. This advantageously minimizes or eliminates the possibility of implants, such as occlusion devices, previously placed at the site, from contacting the electrode and creating a current return path that bypasses the blood or fluid between the etch site on the sacrificial link and the return electrode. Such contact may otherwise preclude electrolysis and coil detachment. The distal most surface of the electrode also may be electrically insulated to minimize the likelihood of endolumenal structures from contacting the electrode.

According to another embodiment of the invention, the most distal surface of the electrode may be adjacent to the distal tip of the catheter. In this arrangement, that most distal surface is electrically insulated to minimize the likelihood of endolumenal structures contacting the electrode.

According to another aspect of the invention, the conductor is embedded in the wall of the tubular member. This advantageously places the conductor or lead outside the lumen so that it does not interfere with the passage of the implant (e.g., an occlusion device such as an embolic coil) as the implant is delivered through the catheter to the desired site. This arrangement also prevents the conductor from contacting the vessel wall.

According to a further feature of the invention, the electrode is positioned so as not to extend radially inward beyond the inner surface of the tubular member that defines the lumen. With this construction, the possibility of the electrode catching the implant or occlusion device as it passes the electrode is largely avoided or eliminated.

The above is a brief description of some of the features and advantages of the present invention. Other features, advantages and embodiments of the invention will be apparent to those skilled in the art from the following description, accompanying drawings and appended claims.

DETAILED DESCRIPTION OF THE INVENTION

Figure 1:
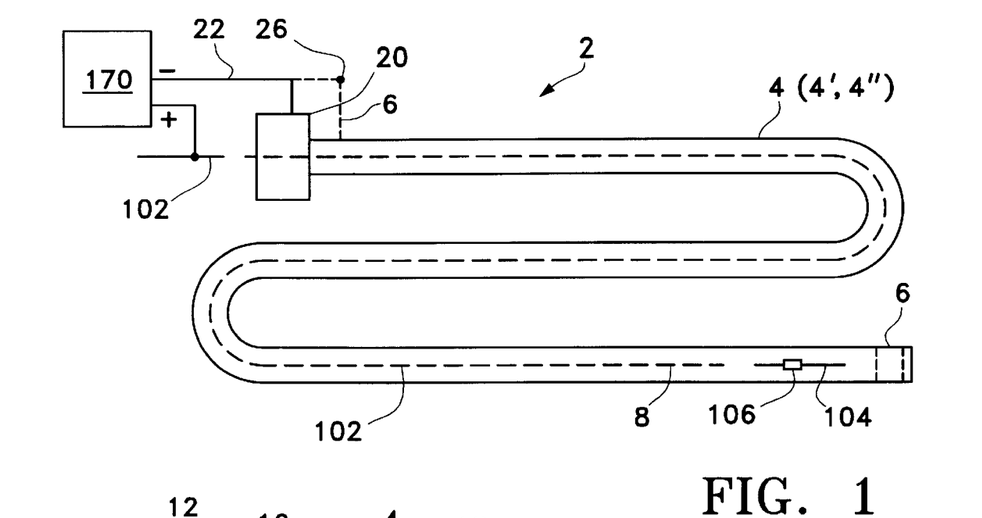
FIG. 1 is a diagrammatic view of an electrolytic detachment system constructed according to the principles of the present invention.

Referring to the drawings in detail wherein like numerals indicate like elements, an implant delivery and electrolytic detachment system 2 constructed according to the principles of the present invention is diagrammatically shown. Referring to FIG. 1, system 2 generally comprises a delivery catheter 4, which includes electrode 6, an implant delivery assembly 8 and power supply 170. Implant delivery assembly 8 generally includes a guidewire (or core wire), an implant and a sacrificial link that couples the implant to the guidewire, as will be described in more detail below.

Figures 2, 3:
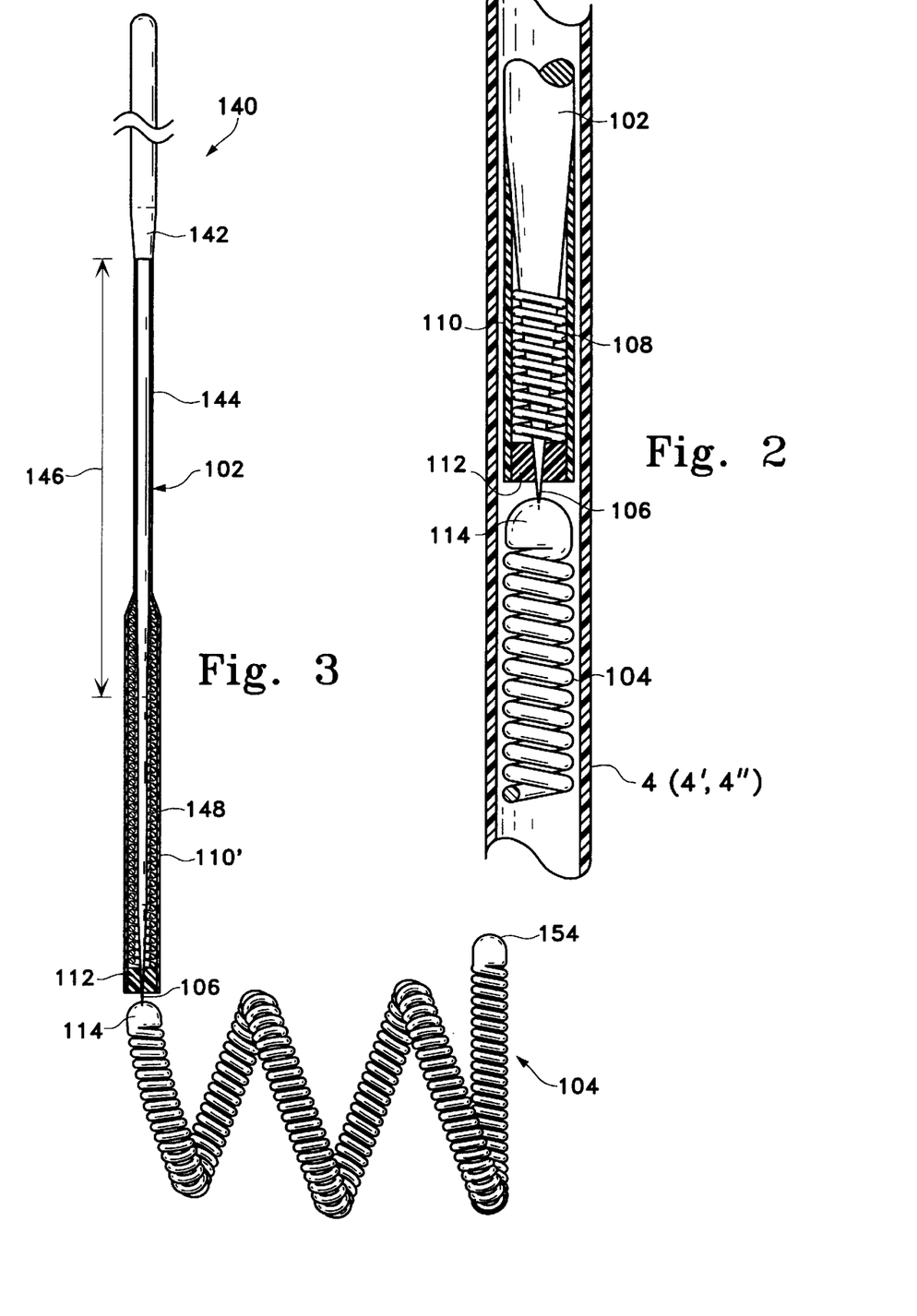
FIG. 2 is an enlarged partial section of the implant delivery assembly shown in FIG. 1, illustrating the interconnection among the guidewire, sacrificial link and implant.
FIG. 3 illustrates a further embodiment of the interconnection shown in FIG. 2.

Referring to FIG. 2, an enlarged view of a portion of implant assembly 8 is shown illustrating the interconnection between the guidewire, sacrificial link and implant for facilitating electrolytic detachment of the implant from the guidewire. Specifically, guidewire 102 tapers at its distal end to a point which is soldered into the proximal end of an implant 104. In the illustrative embodiment, implant 104 is shown as a vasoocclusive device, which in this case is a coil preferably of radiopaque physiologically compatible material such as platinum, tungsten, gold, iridium or alloys of these materials.

Guidewire 102, which preferably is stainless steel, typically is approximately 10–30 mils in diameter and 50–300 cm in length from the entry site outside the body to sacrificial link 106. As shown in FIG. 2, sacrificial link 106 is the exposed portion of guidewire 102 that extends beyond insulator 112. Link 106 is of a material, such as stainless steel, which is susceptible to electrolytic dissolution in blood.

Guidewire 102 preferably is covered with an insulating material from its proximal end to its distal exposed portion which forms sacrificial link 106. Suitable insulating materials include Teflon®, polyurethane, polyethylene, polypropylene, or other suitable polymeric material. In a first embodiment, link 106 is not coated with an electrical insulator. In this case, the length of link 106 preferably is approximately equal to its diameter so that the electrolytic surface present after the vasoocclusive device is released is not substantially greater than would be a circle having the diameter of the link (link diameters, when dealing with aneurysms, may range from about 2–4 mils, for example). This configuration reduces the likelihood of multiple etch sites on the link. Alternatively, link 106 can be coated with a polymer, preferably parylene (polyxylylene), and a UV laser (excimer type) used to cut a circumferential groove, having about a 1–3 mil in width, in the polymer to expose only a small ring of the link and localize the disintegration area. Preferably, the groove is immediately adjacent to the interconnection between the link and implant.

Implant delivery assembly 8 also includes insulators 110 and 112 and coil 108, which is coupled at its proximal end to the guidewire by soldering, for example. Coil 108 is designed to provide some column strength to guidewire 102 while not detrimentally affecting the flexibility of the tapered portion of the guidewire. Obviously, in the area where support coil 108 is soldered to guidewire 102, the coating on the guidewire is not present, allowing the solder to adhere to metal surfaces.

Insulators 110 and 112 are provided at the distal end portion of guidewire 102 and serve to further remove stainless steel coil 108 from contact with the blood during electrolysis. In the illustrative embodiment, insulators 110 and 112 comprise a sleeve and plug, respectively. Preferably, end plug 112 and sleeve 110 are adhesively attached to each other to form an electrically insulating or electrolysis-tight housing about coil 108. End plug 112 and sleeve 110 form a generally planar surface which is generally perpendicular to the axis of the guidewire 102 (FIG. 2). The shape of the surface is not critical except to the extent it allows reasonably free access of the blood to sacrificial link 106. Curved, slotted and other variations of the end surface are also contemplated to be used in this invention. As noted above, the distal end of guidewire 102 is inserted into the solder joint 114 forming the proximal end of vasoocclusive device 104.

Referring to FIG. 3, one suitable configuration for guidewire 102 is shown. In this embodiment, guidewire 102 includes tapered or conical section 142, section 144 which extends along a length of the guidewire designated with reference numeral 146 and section 148. Section 144 gradually narrows down to thinner section 148. Guidewire 102 is delivered to the desired site via a catheter constructed according to the present invention (e.g., catheter 4, 4' or 4") and is typically 50–200 cm in length down to sacrificial link 106. In the arrangement shown in FIG. 3, the distal section of guidewire 102 has an outer sleeve 110', comprising Teflon® or other appropriate insulating material, which is longer than sleeve 110 in FIG. 2.

Preferably, vasoocclusive device 104, when a coil, is prebiased to form a secondary loop or helix superimposed on its primary helical winding configuration when in a relaxed state, as shown in FIG. 3. However, vasoocclusive device 104 preferably is extremely soft and its overall shape is easily deformed. When inserted within a catheter, such as catheter 4 as diagrammatically shown in FIG. 2, vasoocclusive device 104 is easily straightened to lie axially within the catheter. Once ejected from the tip of the catheter, vasoocclusive device 104 may form a shape such as that shown in FIG. 3. Alternatively, device 104 may be constructed to have a different secondary shape or it may be loosely deformed to conform to the interior shape of the aneurysm. The distal end of vasoocclusive device 104 may also have an end plug or tip 154 to prevent punctures of endolumenal structures such as an aneurysm wall when introduced into an aneurysm sac.

Although implant 104 is shown as a vasoocclusive coil, it may take other forms. It can be a vasoocclusive braid, for example. Vasoocclusive device 104 also may be covered or connected with fibrous materials tied to the outside of the coil or braided onto the outer cover of the coil as desired. Such fibrous adjuvants may be found in U.S. patent appl. Ser. No. 5,382,254, to Phelps et al, or in U.S. patent appl. Ser. No. 5,226,911, entitled "Vasoocclusion Coil with Attached Fibrous Elements", the entirety of which are incorporated by reference.

Figure 4:
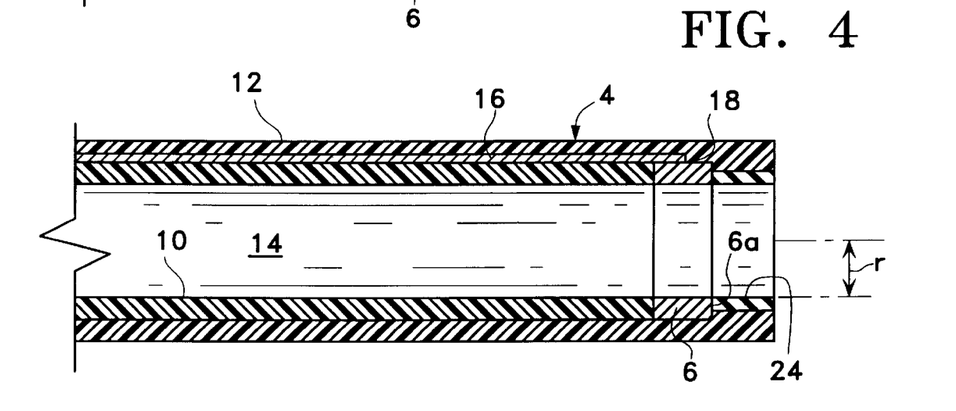
FIG. 4 is an enlarged sectional view of the distal end portion of the catheter shown in FIG. 1 illustrating a return electrode arrangement according to the present invention.

Referring to FIG. 4, a sectional view of delivery catheter 4 is shown in accordance with the present invention. Catheter 4 preferably comprises an elongated tubular member or tube having a laminate structure comprising a pair of concentrically arranged tubular members or tubes 10 and 12. The inner surface or wall of tube 10 defines lumen 14 through which the implant delivery assembly 8 is passed. This construction facilitates positioning or embedding the electrode and conductor within the catheter as will be more fully appreciated from the description below. However, other catheter constructions may be used without departing from the scope of the invention.

In accordance with the present invention, return electrode 6 is provided within catheter 4. The electrode can, for example, comprise copper, platinum, nitinol or alloys thereof. It is important that electrode 6 be positioned within catheter 4 to minimize the risk of or avoid presenting an exposed surface that could interface with endolumenal structures in the electrolysis or detachment zone. In general, the electrode is arranged to minimize the likelihood of electrical contact with such endolumenal structures.

According to one embodiment of the invention, electrode 6 preferably also is positioned or spaced longitudinally inward from the distal tip of catheter 4, as shown in FIG. 4, so that the possibility of any coils (previously delivered to the detachment or electrolysis zone) contacting the electrode and adversely affecting electrolysis is minimized or eliminated. Although the electrode preferably is as close as possible to the distal tip of the catheter to minimize the impedance in the return current path, the most distal surface of the electrode preferably is spaced inwardly from the distal end of the catheter a distance equal to at least one-half the inner radius of lumen 14 to minimize or eliminate interference with other coils as noted above. In other words, the electrode preferably is exposed only to the internal lumen of the catheter, and is as distal as possible without conducting at the catheter tip.

Figure 4A:
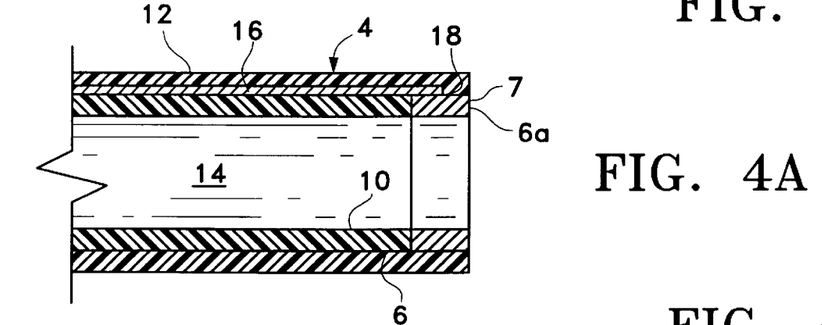
FIG. 4A shows another embodiment of the return electrode arrangement of FIG. 4.

According to another embodiment of the invention, the most exposed surface, such as distal side surface 6a illustrated in the example shown in FIG. 4A, is electrically isolated. This arrangement also is believed to provide the desired results and can be accomplished, for example, by applying a coating or thin film 7 of insulation material to distal or transversely extending surface 6a of electrode 6 as would be apparent to one of ordinary skill in the art. The insulation also can be extended proximally along a portion of the inner circumferential surface of electrode 6.

With the above-described electrode positioning, the fluid (preferably a saline solution) flowing in the delivery catheter will provide a reproducible impedance path from the internal electrode to the detachment zone where the sacrificial link resides and, thus, reduce detachment time variability.

In the illustrative embodiment, electrode 6 is annular and positioned inside outer tube 12 and adjacent to the distal end of inner tube 10. The inner diameter of annular electrode 6 preferably is the same as the inner diameter of inner tube 10 so that the electrode and inner tube 10 present a continuous, nonobstructed, smooth surface to prevent implant or coil 104 from touching that surface when being delivered through lumen 14 to the target site. The annular configuration also advantageously provides a large exposed electrode surface that enhances current flow efficiencies. Although a particular electrode configuration has been shown, it should be understood that other configurations can be used. Generally, a large electrode surface area is desired as it increases current flow efficiencies by avoiding too large a current density passing therethrough. For example, a segmented electrode can be used that is spaced in the circumferential direction along the inner surface of the catheter in the same position as shown in FIGS. 4 or 4A.

Catheter 4 is further provided with a conductor 16. Referring to FIG. 4, conductor 16 is in the form of wire and has a distal end that is coupled, for example by soldering, to electrode 6 at the general location indicated by reference numeral 18. Conductor 16 extends from electrode 6 between tubular members 10 and 12 to proximal end portion of catheter 4 where it can be electrically connected to power supply 170 either directly or with a lead as would be apparent to one of ordinary skill. For example, conductor 6 can extend through a radial portion of the proximal portion of catheter 4 adjacent to hub 20 as shown in FIG. 1 and then be coupled to lead 22 (e.g., at reference point 26) which is electrically coupled to the negative terminal or cathode of the power supply. Alternatively, conductor 6 can extend into a conventional hub assembly 20 (diagrammatically shown in FIG. 1) where the conductor 6 is electrically coupled to lead 22 via a connection in the hub.

Delivery catheter 4 preferably is manufactured in the following way which is provided for illustrative purposes, but not intended to limit the invention. Inner tube 10 and electrode 6 are positioned on a mandrel having a diameter slightly less than the inner diameter of inner tube 10 and electrode 6. Electrode 6 is positioned immediately adjacent the distal end of inner tube 10, as shown in FIG. 4. The conductor 16 is then coupled to the electrode and extended toward the proximal end portion of the catheter, where it eventually is interconnected with hub 20, or extended radially through tube 12 adjacent to hub 20 as described above. Referring to FIG. 4, outer tube 12 is then moved over the electrode toward the distal end of inner tube 10 and then toward the proximal portion of catheter 4, where it is coupled to hub 20. In this manner, conductor or wire 16 is embedded in the catheter wall and prevented from entering lumen 14, where it could otherwise interfere with the delivery of coil 104. At the very distal end of the catheter, a filler 24 comprising thermoplastic material, for example, is provided to maintain an essentially constant lumen diameter and embed the distal side surface 6a of electrode 6 in the catheter to preclude its exposure to the endolumenal environment.

Figures 5A, 5B:
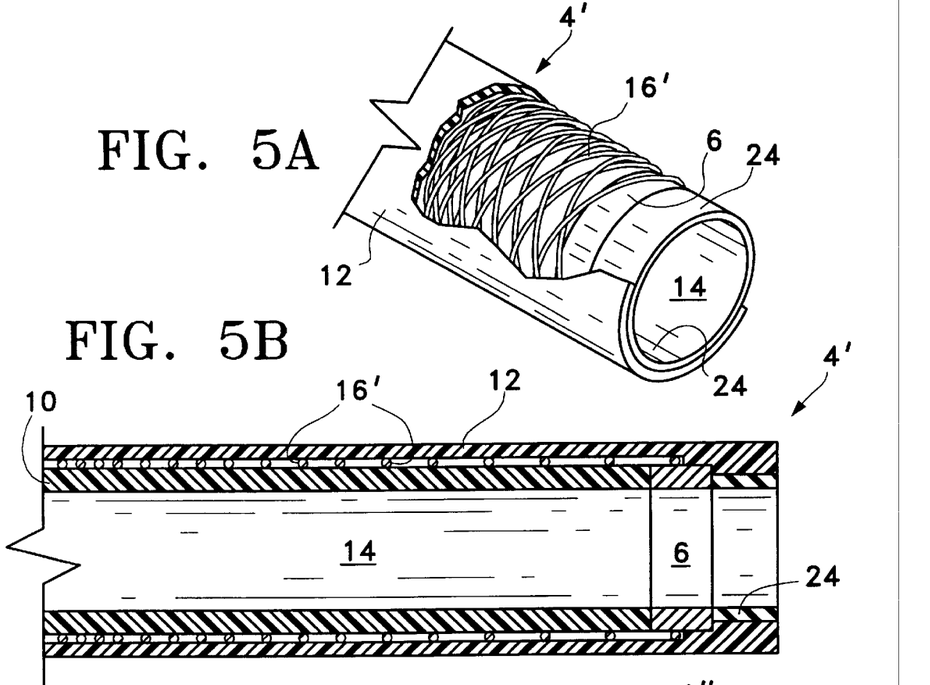
FIGS. 5A and 5B show a further embodiment of the catheter of the present invention.

Referring to FIGS. 5A and 5B, a further embodiment of the invention is shown. In this embodiment, catheter 4' is the same as catheter 4 except that the conductor, designated with reference numeral 16', is a generally tubular braided member (e.g., having a construction like a "Chinese finger"). Conductor 16' preferably is positioned between tubes 10 and 12 for the reasons discussed above. In addition to providing a coupling from the electrode to the power supply, the braided construction allows the conductor to provide the catheter with variable stiffness simply by varying the mesh size of the braid along the length of the conductor. In the preferred embodiment, the mesh size of the braid progressively increases toward the distal end of the conductor so that the catheter flexibility progressively increases toward the distal tip. This allows the catheter to maneuver into very small, complex vessel structures.

Figures 6A, 6B:
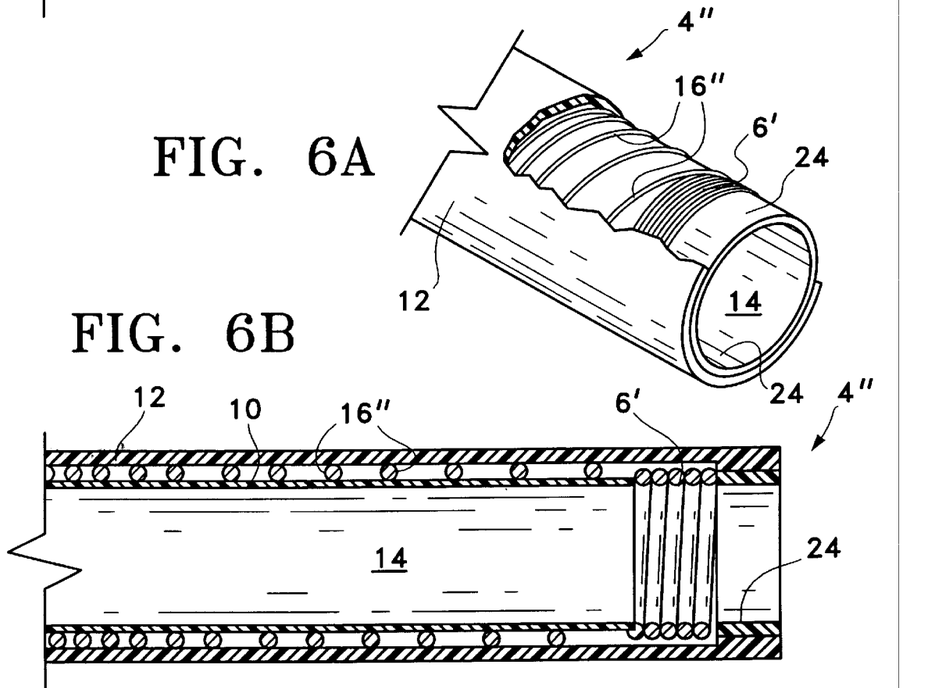
FIGS. 6A and 6B show yet another embodiment of the catheter of the present invention.

In another embodiment of the invention, the coil is configured as a coil as shown in FIGS. 6A and B and designated with reference character 16". In this embodiment, the coil pitch preferably increases toward the distal tip to progressively increase the flexibility of the catheter in the same direction to enhance catheter maneuverability as noted above. Coil 16" can be coupled to electrode 6. Alternatively, the distal portion of coil 16" can be substituted for electrode 6 as shown in FIG. 6B. That is, in a preferred embodiment, coil portion 16", which extends distally of tube 10, forms the electrode.

Figure 7:
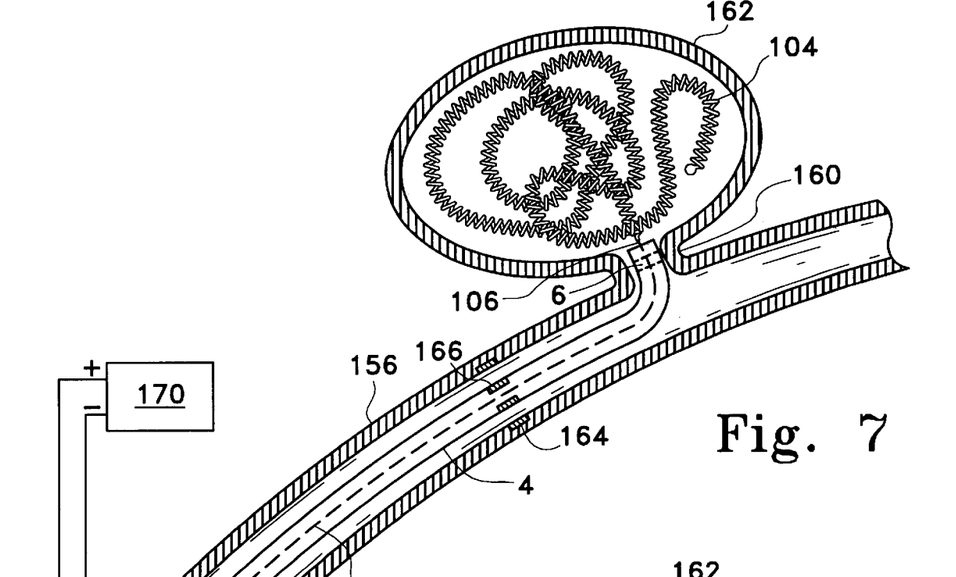
FIGS. 7 and 8 schematically depict the method for deploying an occlusion device according to the present invention.

FIG. 7 shows the placement of an occlusion device described above within an aneurysm. The procedure for placing an embolic device is typically practiced under fluoroscopic control with local anesthesia. A transfemoral catheter is utilized to treat a cerebral aneurysm and is usually introduced at the groin. The physician guides the distal tip of the catheter to the target site. The embolic device is then inserted into the catheter. Using a fluoroscope, the physician guides the device to the desired position before separation is initiated. When the vasoocclusive device 104 is platinum, it is not effected by electrolysis. When the guidewire and pertinent portions of the supporting coils at the distal tip of the guidewire are adequately coated with insulating coverings, only the exposed portion at the sacrificial link 106 is effected by the electrolysis.

Returning to FIG. 7, catheter 4 is positioned in a vessel 156 with the tip of catheter 4 placed near neck 160 of aneurysm 162. A vasoocclusive device, such as device 104, is fed into aneurysm 162 at least until sacrificial link 106 is exposed beyond the distal tip of the catheter 158. The guidewire and catheter can be provided with radiopaque markers to facilitate observation of the relative positions of the guidewire and catheter distal ends as disclosed in U.S. Pat. No. 5,354,295, which is hereby incorporated herein by reference. Alternatively, the catheter and guidewire may be provided with radiopaque markers, such as markers 164 and 166, that are arranged so that they become aligned when sacrificial link 106 is just outside the distal tip of the catheter as diagrammatically shown in FIG. 7.

A positive electric current of approximately 0.1–10 milliamps, preferably about 1 milliamp, at 0.1–6 volts, is applied to guidewire 102 (shown in dashed line) via DC power supply 170 to form a thrombus within aneurysm 162 and dissolve sacrificial link 106. As shown in FIGS. 5 and 6, the positive terminal of power supply 170 is attached to the proximal end of guidewire 102 and, thus, to link 106. Negative or return electrode 6 is coupled to the negative terminal of power supply 170, as described above.

Figure 8:
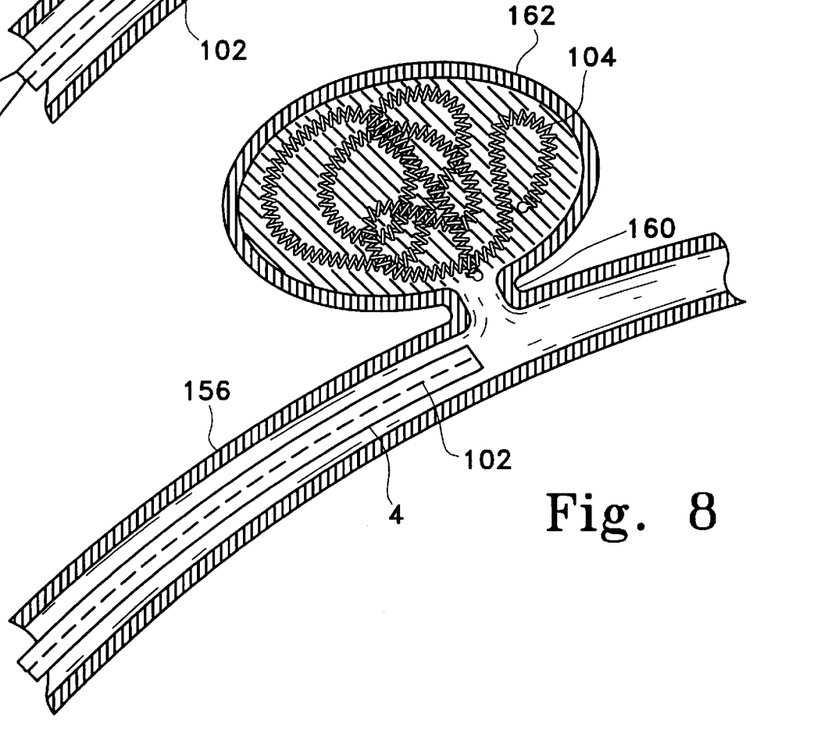

After a vasoocclusive device has been properly placed inside the aneurysm 162, the power is delivered to link 106 and a solution, preferably a saline solution, is delivered through the catheter to enhance current flow from link 106 into catheter 4 to electrode 6. After sacrificial link 106 is completely dissolved by electrolytic action, typically within 1–10 minutes, thereby detaching device 104 from guidewire 102, guidewire 102 is removed from catheter 4 and from vessel 156. Additional vasoocclusive devices may be placed in aneurysm 162 along with previously detached devices 104 until aneurysm 162 is occluded as shown in FIG. 8. At this point, guidewire 102 and catheter 158 are withdrawn.

A detachment detection system, such as disclosed in PCT application number PCT/US95/02635 entitled "Endovascular Embolic Detachment Detection Method," may be used with the invention to determine when the implant becomes detached so that the power supply can be shut down. In general, DC power with AC superposition is provided to facilitate both electrolysis and detection.

The DC power input facilitates electrolysis of link 106 and, thus, detachment of the coil, while the AC power provides a signal to monitor and detect detachment. More specifically, the voltage or current amplitude of the AC signal is monitored so that the DC power input can be interrupted in response to detecting a sudden change in the AC signal amplitude. If the DC power source is of a constant current design, the voltage amplitude of the AC signal would be monitored. If the DC source has a constant voltage output, the current amplitude of the AC signal provides the desired change. A preferred power supply and embolic device detection circuit (EDDC) is described below.

Figure 9:
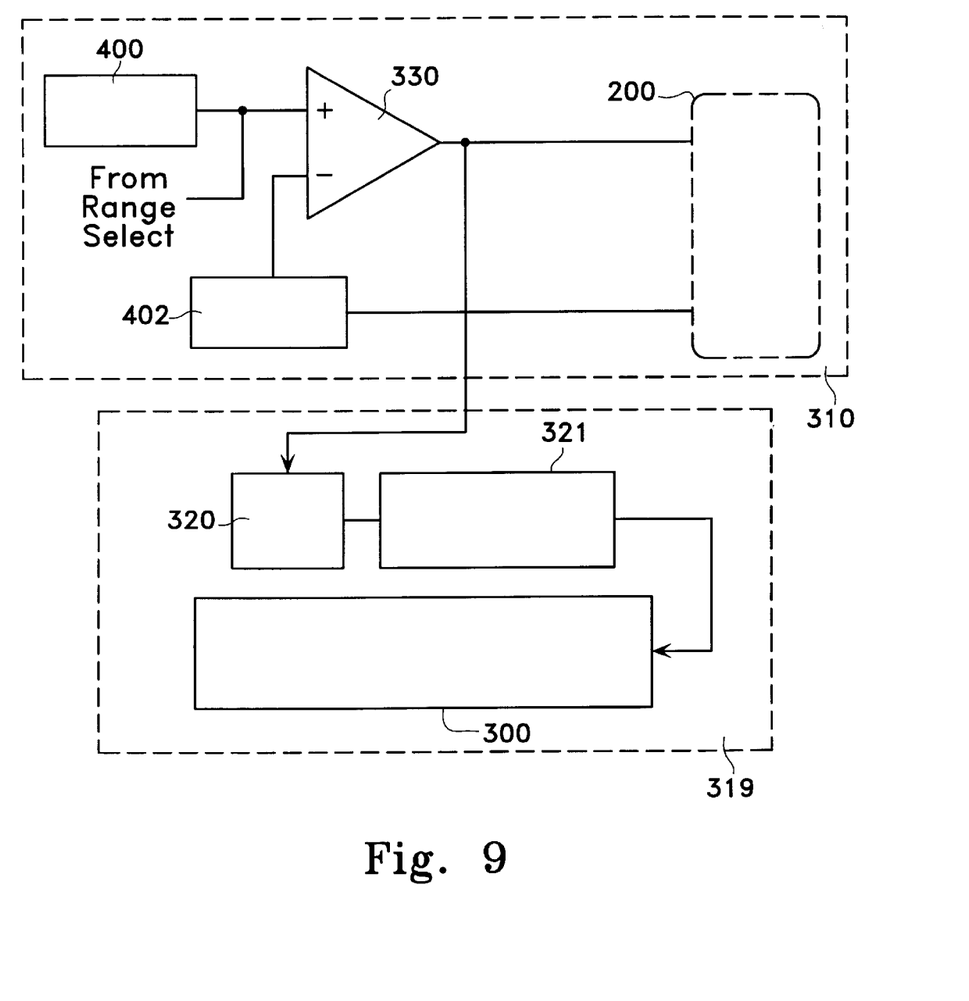
FIG. 9 is a block diagram of a power drive delivery and detection circuit for detecting electrolytic separation of an occlusion device.

Referring to FIG. 9, a constant current drive circuit and feedback loop 310 and an EDDC 319 for inducing and detecting the electrolytic separation of an occlusion device from a delivery member or guidewire are shown. The EDDC includes an AC impedance monitoring circuit and a circuit for detecting changes in the monitored impedance which can comprise microprocessor 300 as will be described in more detail below. The power supply and detection circuit (310, 319) provide a means to supply DC power with AC superposition and directly monitor the AC impedance by observing the reaction of amplifier 330 in response to the change in AC impedance.

Figure 10:
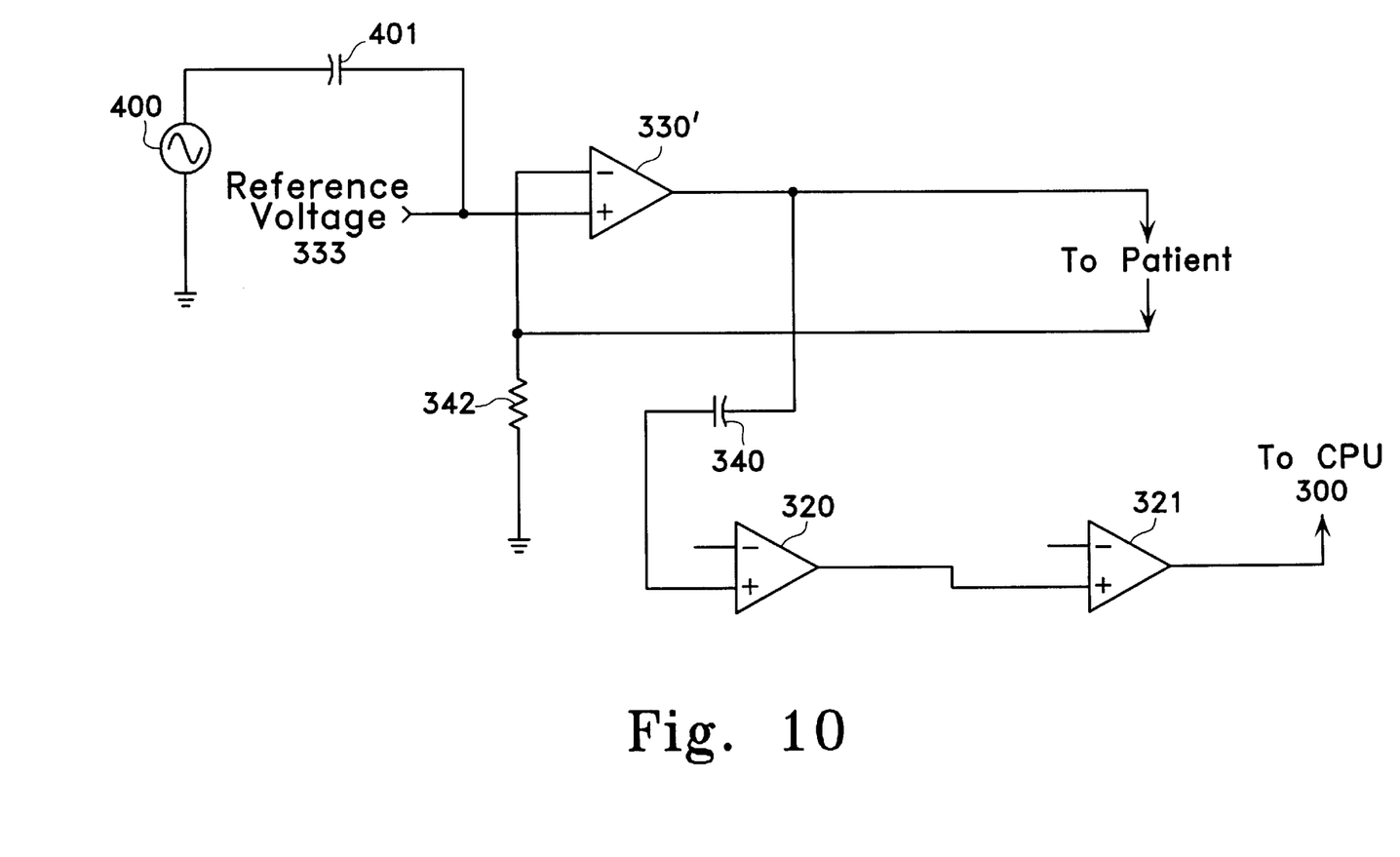
FIG. 10 is a schematic representation of the block diagram of FIG. 9.

Referring to FIG. 10, AC signal source 400 is coupled to the reference input of amplifier 330 so as to modulate the output current (i.e., provide AC superposition on the DC current). For purposes of example, a 31.25 kHz 100 mV peak-to-peak sine wave has been found to be a suitable input to the amplifier. Capacitor 401 is provided between AC signal source 400 and amplifier 330 to isolate DC bias from the AC signal input. Reference Voltage 333 and current sense resistor 342 and amplifier 330 comprise a constant current drive circuit. One suitable amplifier is a TI2274N amplifier manufactured by Texas Instruments.

In operation, an AC signal is provided to the non-inverting input of amplifier 330 where it is summed with the DC current reference. DC current with AC superposition is output from amplifier 330 and sent to the sacrificial link (e.g., link 106 shown in FIG. 2,) which is positioned in patient 200. The DC and AC current paths branch. The DC current flows from the sacrificial link without passing through the coil, while the AC signal continues through the coil. These current paths rejoin at return electrode 6 (TIM: Please Confirm) and continue to AC and DC feedback loop 402. The AC signal is monitored at the output of the constant current amplifier where a measurement of AC impedance can be made through EDDC 319.

The amplitude of the AC signal is monitored through pick-off capacitor 340 (FIG. 10), in this case, a 0.1 microfarad monolithic capacitor. The AC signal from capacitor 340 is then amplified in the AC signal amplifier 320, and is rectified and the peak detected in the AC to DC rectifier 321. The DC signal, the level of which is representative of the amplitude of the AC voltage of constant current amplifier 330 is then sent to the microprocessor (CPU) 300 for monitoring and analysis as described below.

The AC signal, which in the illustrated embodiment described above is voltage, is monitored by sampling the level of the amplified DC signal every 10 to 250 milliseconds, preferably every 50 to 200 milliseconds, and constantly averaging the signal every 5 to 50 samples, preferably every 10–20 samples or every 0.5–10 seconds, preferably every 2–6 seconds. In this manner, the CPU can accurately determine the instant the occlusion device detaches as discussed below.

When the occlusion device detaches, constant current amplifier 330 instantly reacts to the change in AC impedance. The voltage amplitude of the AC waveform increases in an attempt to maintain the constant AC current set at the non-inverting input. During this period the amplified EDDC signal will show a sudden voltage increase of greater than 20%, preferably an increase of greater than 30% of the average level for the procedure. This sudden voltage increase reliably detects the dissolution of the junction between the embolic device and the guidewire.

When the sudden voltage decrease is detected, the microprocessor immediately halts current flow, and no further electrolysis can occur. Using fluoroscopy, the physician can verify that detachment has occurred. If detachment is incomplete and further electrolysis is necessary, the procedure can be resumed by pressing the current-select switch on the front panel. If detachment is verified, the physician can turn off the power supply and withdraw the guidewire. If necessary, another coil can be placed at the site and the power supply started again. If no action is taken, the power supply will automatically turn itself off after 15 minutes.

Throughout this application, various publications, patents and patent applications are referred to by an identifying citation. The disclosures of these publications, patents and published patent applications are hereby incorporated by reference into this application.

The above is a detailed description of particular embodiments of the invention. It is recognized that departures from the disclosed embodiment may be made within the scope of the invention and that many alterations and modifications may be made by those having ordinary skill in the art without departing from the spirit and scope of the invention set out in the claims. The full scope of the invention is set out in the claims that follow and their equivalents.

I claim as my invention:

1. A catheter for introducing a guidewire having a detachable implant coupled thereto via an electrolytically disintegratable link that is coupled to an anode of a power supply having said anode and a cathode, said catheter comprising:

an elongated tubular member having an outer surface, proximal and distal end portions and an inner surface defining a lumen;

an electrode secured to said distal end portion and having a radial electrode outer surface that is electrically shielded and a radial electrode inner surface that faces and communicates with said lumen, said electrode positioned to provide a reproducible impedance path from said electrode to said electrolytically disintegratible link through an ionic solution; and a conductor which is electrically coupled to said electrode, which extends proximally from said electrode externally of said lumen, and which is adapted for coupling to the cathode of said power supply such that when said electrolytically disintegratable link is placed in an ionic solution and positive current from the power supply is provided to said link, current from said link may return to the cathode of said power supply via said electrode, allowing electrolytic disintegration of said link to occur to detach said implant.

2. The catheter of claim 1 wherein said electrode has a most distal surface, said distal surface being electrically insulated.

3. The catheter of claim 1 wherein said electrode is ring shaped.

4. The catheter of claim 1 wherein said electrode comprises metal.

5. The catheter of claim 1 wherein said elongated tubular member comprises a laminate construction including first and second tubes, said conductor being disposed between said first and second tubes.

6. The catheter of claim 1 wherein said distal end portion of said elongated tubular member is electrically non-conductive and said electrode is disposed within and is circumferentially covered by said outer surface of the elongated tubular member in the vicinity of the distal end portion.

7. The catheter of claim 6 wherein said distal end portion of said elongated tubular member includes a distal tip, said electrode being spaced inwardly from said distal tip.

8. The catheter of claim 7 wherein said electrode has a most distal surface, said most distal surface being electrically isolated.

9. The catheter of claim 7 wherein said electrode is spaced inwardly from said distal tip a distance of at least one-half the radius of the lumen measured at said distal tip.

10. The catheter of claim 9 wherein said electrode does not extend radially inward beyond said inner surface of said elongated tubular member.

11. The catheter of claim 6 wherein said electrode does not extend radially inward beyond said inner surface of said elongated tubular member.

12. The catheter of claim 6 wherein said conductor is embedded in said elongated tubular member.

13. The catheter of claim 12 wherein said conductor is in the form of a wire.

14. The catheter of claim 12 wherein said conductor comprises a tubular braided member.

15. The catheter of claim 14 wherein said tubular braided member has an end portion generally aligned with said distal end portion of said elongated tube, said braided member end portion having a mesh size that is greater than at least a substantial extent of the remaining portion of said braided member.

16. The catheter of claim 14 wherein said tubular braided member has multiple flexibilities along its length with the distal end portion of said braid having a relatively high flexibility.

17. The catheter of claim 12 wherein said conductor comprises a coil.

18. The catheter of claim 15 wherein said coil has a varying pitch and the pitch and the distal end portion of the coil are relatively large.

19. The catheter apparatus of claim 18 wherein said distal end portion of said elongated tubular member is electrically non-conductive and said electrode is disposed within and is circumferentially covered by said outer surface of the elongated tubular member in the vicinity of the distal end portion.

20. The apparatus of claim 19 wherein said electrode is spaced longitudinally inward from said distal end of said elongated tubular member.

21. The apparatus of claim 19 wherein said conductor is embedded in said tubular member.

22. The apparatus of claim 21 wherein said elongated tubular member comprises a laminate construction including first and second tubes, said conductor being disposed between said first and second tubes.

23. The apparatus of claim 20 wherein said electrode has a most distal surface, said most distal surface being electrically insulated.

24. The mammalian implant delivery system of claim 23 wherein said distal end portion of said elongated tubular member is electrically non-conductive and said electrode is disposed within and is circumferentially covered by said outer surface of the elongated tubular member in the vicinity of the distal end portion.

25. The system of claim 24 wherein said electrode is spaced longitudinally inward from said distal end.

26. The system of claim 25 wherein said electrode has a most distal surface, said most distal surface being electrically insulated.

27. The catheter apparatus of claim 26 wherein said tubular member comprises a polymeric material.

28. The system of claim 24 further including a conductor that is embedded in said tubular member, said conductor having a first portion electrically coupled to said electrode and a second portion electrically coupled to said cathode.

29. The system of claim 28 wherein said elongated tubular member comprises a laminate construction including first and second tubes, said conductor being disposed between said first and second tubes.

30. The mammalian implant delivery system of claim 29 wherein said tubular member comprises a polymeric material.

31. A mammalian implant delivery system comprising:

a power supply having an anode and a cathode;

a catheter comprising a tubular member having an outer surface, a proximal and distal end portion, and an inner surface defining a lumen;

an electrode secured to said distal end portion and having a radial electrode outer surface that is electrically shielded and a radial electrode inner surface that faces and communicates with said lumen, said electrode positioned to provide a reproducible impedance path from said electrode to an electrolytically disintegratible link through an ionic solution;

a conductor having a first portion electrically coupled to said electrode and a second portion electrically coupled to said cathode;

a detachable implant suitable for mammalian implantation;

a delivery member disposed in said catheter for delivering the detachable implant to a region in the mammal;

said electrolytically disintegratible link coupling said delivery member to said implant, said link being electrically coupled to said anode.

32. The system of claim 31 wherein said electrode has a most distal surface, said most distal surface being electrically insulated.

33. The system of claim 31 wherein said electrode does not extend radially inward beyond said inner surface.

34. The catheter of claim 32 wherein said tubular member comprises a polymeric material.

35. A catheter apparatus for use with a detachable implant comprising:

a power supply having an anode and a cathode;

an elongated tubular member having an outer surface, a proximal and distal end portion, and an inner surface defining a lumen;

an electrode secured to said distal end portion and having a radial electrode outer surface that is electrically shielded and a radial electrode inner surface that faces and communicates with said lumen, said electrode positioned to provide a reproducible impedance path from said electrode to an electrolytically disintegratible link through an ionic solution; and an elongate conductor having a first conductor portion electrically coupled to said electrode and a second conductor portion coupled to said cathode and which extends between said electrode and said cathode externally of said lumen.

36. The apparatus of claim 35 wherein said electrode has a most distal surface, said most distal surface being electrically insulated.

37. The apparatus of claim 35 wherein said electrode does not extend radially inward beyond said inner surface.

* * * * *